United States Patent [19]

Bellussi et al.

[11] Patent Number: 5,246,690

[45] Date of Patent: Sep. 21, 1993

[54] SYNTHETIC, CRYSTALLINE, POROUS MATERIAL CONTAINING SILICON OXIDE, TITANIUM OXIDE AND ALUMINUM OXIDE

[75] Inventors: Giuseppe Bellussi, Piacenza; Aldo Giusti, Lucca; Antonio Esposito; Franco Buonomo, both of San Donato Milanese, all of Italy

[73] Assignees: Eniricerche S.p.A., Milan; Enichem Sintesi S.p.A., Palermo; Snamprogetti S.p.A., Milan, all of Italy

[21] Appl. No.: 740,860

[22] Filed: Jul. 31, 1991

Related U.S. Application Data

[63] Continuation of Ser. No. 545,780, Jun. 28, 1990, abandoned, which is a continuation of Ser. No. 434,557, Nov. 8, 1989, abandoned, which is a continuation of Ser. No. 943,543, Dec. 17, 1986, abandoned.

[30] Foreign Application Priority Data

Dec. 19, 1985 [IT] Italy .............................. 23291 A/85

[51] Int. Cl.$^5$ .............................................. C01B 33/34
[52] U.S. Cl. ..................................... 423/705; 423/713; 423/DIG. 22
[58] Field of Search ................ 423/326, 328, 329, 330, 423/705, 713, DIG. 22; 502/77

[56] References Cited

U.S. PATENT DOCUMENTS

| | | | |
|---|---|---|---|
| 4,061,724 | 12/1977 | Grose et al. | 423/329 |
| 4,707,345 | 11/1987 | Lok et al. | 423/328 |
| 4,831,202 | 5/1989 | Giusti et al. | 423/328 |

Primary Examiner—R. Bruce Breneman
Attorney, Agent, or Firm—Shea & Gould

[57] ABSTRACT

A crystalline, porous, synthetic material is disclosed, together with its related preparation process.

Such a material of zeolitic character, containing silicon, titanium and aluminum oxides, corresponds, in its calcined and anhydrous state, to the following empirical formula:

$$p\ HAlO_2 \cdot q\ TiO_2 \cdot SiO_2$$

wherein p has a value greater than zero and lower than or equal to 0.050, q has a value greater than zero and lower than or equal to 0.025, and the H$^+$ of HAlO$_2$ can be at least partly replaceable or replaced by cations.

18 Claims, 2 Drawing Sheets

SYNTHETIC, CRYSTALLINE, POROUS MATERIAL CONTAINING SILICON OXIDE, TITANIUM OXIDE AND ALUMINUM OXIDE

This application is a continuation of U.S. patent application Ser. No. 07/545,780, filed Jun. 28, 1990, now abandoned, which in turn is a continuation of U.S. patent application Ser. No. 07/434,557, filed Nov. 8, 1989, now abandoned, which in turn is a continuation of U.S. application Ser. No. 06/943,543, filed Dec. 17, 1986, now abandoned.

The present invention relates to a synthetic material containing silicon oxide, titanium oxide and aluminum oxide, having a crystalline, porous, structure of zeolitic character and to the process for the preparation of such a material.

Such a material is structurally similar to ZSM-5 zeolite as disclosed in U.S. Pat. No. 3,702,886 patent, formally constituted, in its calcined and anhydrous form, by $M_{2/n}O, SiO_2, Al_2O_3$ (with M=cation with n valency).

Other synthetic materials, structurally correlated to ZSM-5 zeolite are known, such as the one as disclosed in U.S. Pat. No. 4,061,724 patent, formally constituted, in its calcined and anhydrous form, by $SiO_2$; the one as disclosed in BE-886,812 patent, formally constituted, in its calcined and anhydrous form, by $SiO_2$ and $TiO_2$; and the one as disclosed in EP 77,522 patent application, formally constituted by silicon, aluminum and titanium oxides.

A novel synthetic zeolite has been found now, which we'll denominate "titanium-aluminum-silicalite", structurally similar to silicalite, which can be used either as molecular sieve or as ion exchanger, or as catalyst in the following reactions: cracking, selectoforming, hydrogenations and dehydrogenations, oligomerizations, alkylations, isomerizations, dehydrations of oxygen-containing organic compounds—selective hydroxylations of organic substrates by $H_2O_2$ (oxidation of olefins, hydroxylations of aromatics).

The synthetic, crystalline, porous material of zeolitic character, containing silicon, titanium and aluminum oxides, which is the object of the present invention, corresponds, in its calcined and anhydrous state, to the following empirical formula:

$$p\ HAlO_2 \cdot q\ TiO_2 \cdot SiO_2$$

wherein p has a value higher than zero and lower than or equal to 0.050 and q has a value higher than zero and lower than or equal to 0.025, and the $H^+$ of $HAlO_2$ can be at least partly replaceable or replaced by cations.

The passage from a cationic form to another cationic form can be performed by any customary exchange processes of the known art.

The synthetic material in accordance with the present invention results crystalline on X-ray examination.

Such an examination has been carried out by means of a powder diffractometer, equipped with an electronic impulse counter system, by using CuK-α radiation. For the computation of the intensity values, the peak heights have been measured, and their percent heights relatively to the most intense peak have been computed.

The main reflections for the calcined and anhydrous product are characterized by the following d values (wherein d is the interplanar distance):

| d (Å) | Relative Intensity |
|---|---|
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw |

(wherein: vs = very strong; s = strong; m = medium; mw = medium-weak).

Such a diffraction spectrum is essentially similar to that of ZSM-5 and consequently of the other zeolites structurally correlated to ZSM-5, which have been mentioned in the introduction.

The material disclosed by ourselves shows an I.R. spectrum characterized by the following most representative values of wn (wherein "wn" is the wave number):

| wn cm$^{-1}$ | Relative Intensity |
|---|---|
| 1220–1230 | w |
| 1080–1110 | s |
| 965–975 | mw |
| 795–805 | mw |
| 550–560 | m |
| 450–470 | ms |

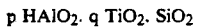

(wherein: s = strong; ms = medium-strong; m = medium; mw = medium-weak; w = weak).

BRIEF DESCRIPTION OF THE DRAWINGS

In FIG. 1 the I.R. spectrum is shown of the calcined and anhydrous zeolitic material of the present invention, wherein on the abscissae and wave number in cm$^{-1}$ and on the ordinates the percent transmittance are expressed.

In FIG. 2 the I.R. spectrum of ZSM-5, or of similar structure, is shown.

In FIG. 3, the I.R. spectrum of a product of comparison Example 11 is shown wherein the $M+/SiO_2$ molar ratio is 0.04 and the crystallization time is 96 hours.

In FIG. 4, a chart is depicted, which sets forth the dependence of the maximum amounts of titanium (shown as $SiO_2/TiO_2$ molar ratio) and of aluminum (shown as $SiO_2Al_2O_3$ molar ratio) which can be obtained in the end product. The I.R. spectrum of FIG. 1 is essentially similar to that of the zeolite as disclosed in BE-886,812, patent whilst it is considerably different from that of ZSM-5 (or from similar structures), as shown in FIG. 2. It can be observed that in this latter spectrum the band at 965–975 cm$^{-1}$, which is characteristic of titanium silicalite of BE-886,812, and of titanium-aluminum-silicalite, does not appear.

Figure 1:
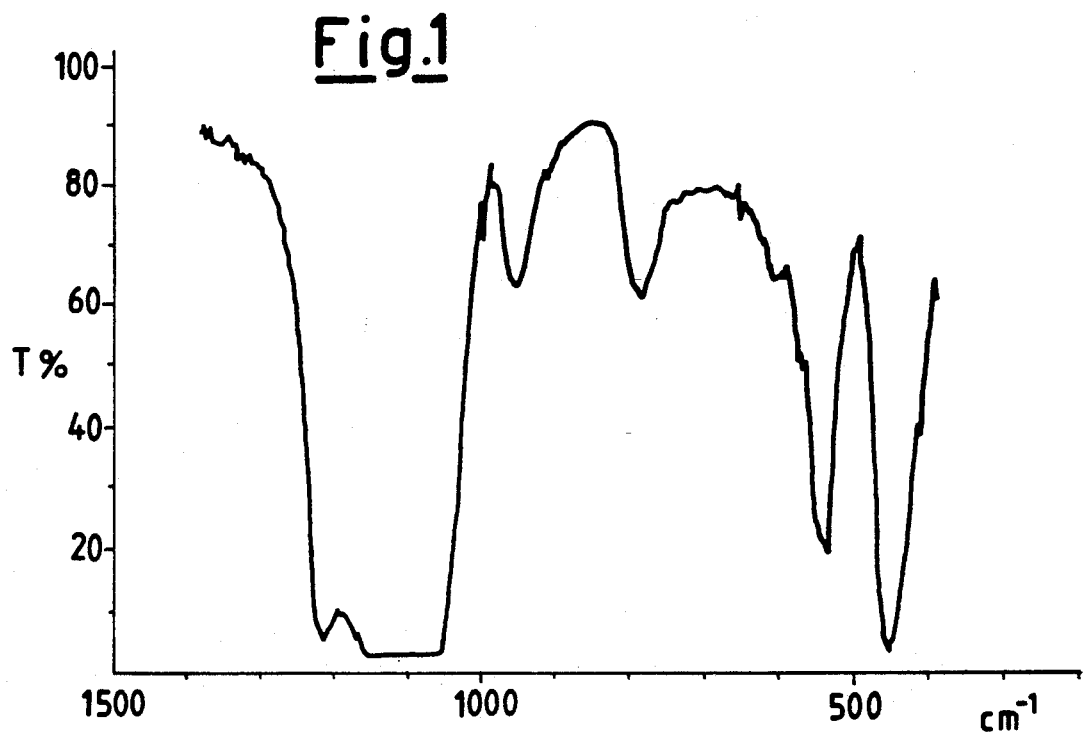
FIG. 1 is an IR spectrum of the claimed invention.
Figure 2:
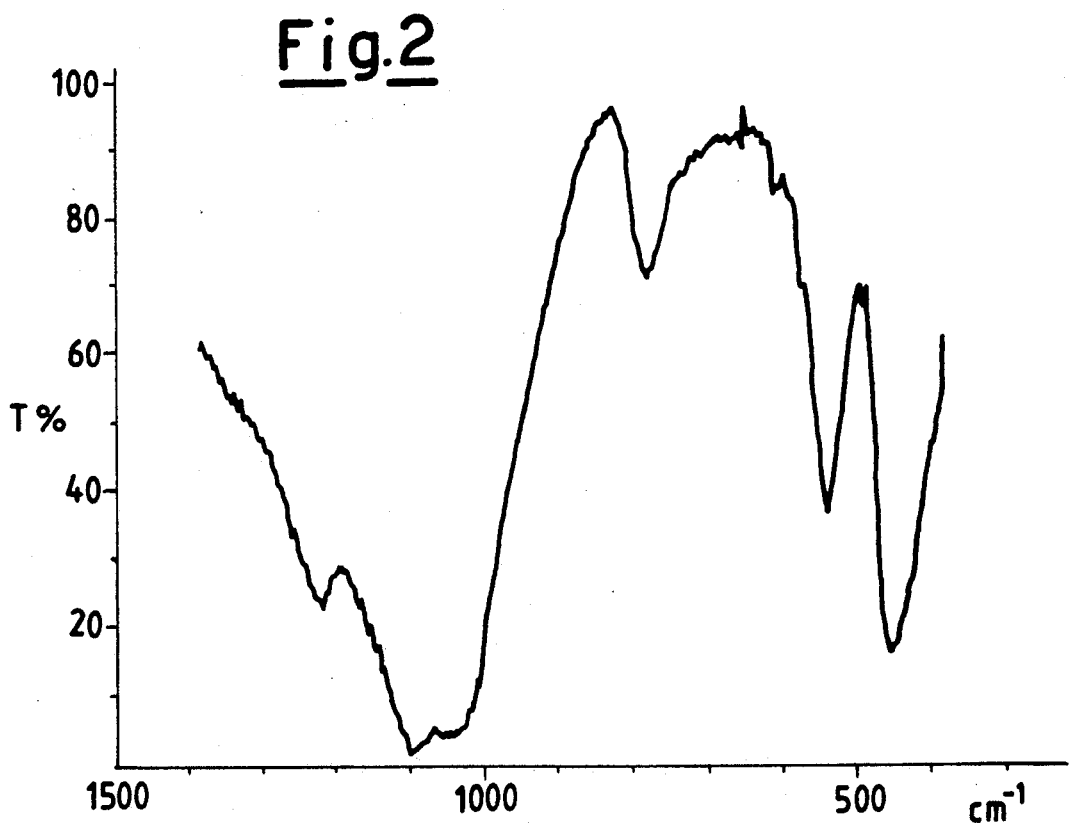
FIG. 2 is an IR spectrum of ZSM-5

Summarizing, the material as disclosed by ourselves is different from ZSM-5 of U.S. Pat. No. 3,702,886, as for both its empirical formula and its I.R. spectrum; relatively to the zeolite of BE-886,812 patent as to its empirical formula; and relatively to the zeolite of EP-77,522 as to its I.R. spectrum.

Furthermore, the use of the subject material of the present invention as a catalyst in the above listed reactions is a further confirmation of the difference of our product relatively to those of the prior art.

In fact, both ZSM-5 of U.S. Pat. No. 3,702,886, and the zeolite of EP-77,522 are used as catalysts in such reactions as dehydrations of oxygenated organic compounds, cracking, selectoforming, hydrogenations and dehydrogenations, oligomerizations, alkylations, isomerizations, but they result inactive in the reactions between organic substrates and $H_2O_2$ (hydroxylation of phenol to diphenols, oxidation of olefins), whilst the zeolite of BE-886,812 results inactive for the first reactions and active for the last ones; to the contrary, our zeolite is active for all of the above mentioned reactions.

A second object of the present invention is the preparation process for the obtainment of the crystalline, porous, synthetic material as defined above.

Said process is characterized in that under hydrothermal conditions a derivative of silicon, a derivative of titanium, a derivative of aluminum and a nitrogenous organic base are reacted, with an $SiO_2/Al_2O_3$ molar ratio of the reactants greater than 100, preferably comprised within the range of from 300 to 400, an $SiO_2/TiO_2$ molar ratio of the reactants greater than 5, preferably comprised within the range of from 15 to 25, an $H_2O/SiO_2$ molar ratio of the reactants preferably comprised within the range of from 10 to 100, more preferably of from 30 to 50, possibly in the presence of one or more salts and/or hydroxides of alkali or alkali-earth metals, with an $M/SiO_2$ molar ratio (wherein M is the alkali or alkali-earth cation) of the reactants lower than 0.1, preferably lower than 0.01, or equal to zero.

In the empirical formula of the material, the aluminum has been indicated in the $HAlO_2$ form, to underline that the material is in the $H^+$ form. When speaking of the ratios between the various reactants, we use, for aluminum, the $Al_2O_3$ form, which is the most usual.

The silicon derivative is selected from silica gel, silica sol and alkyl silicates, among which, preferably, tetraethyl silicate; the titanium derivative is selected from titanium salts, such as, e.g., its halides, and organic titanium derivatives, such as, e.g., alkyltitanates, preferably tetraethyl titanate; the aluminum derivative is selected from aluminum salts, such as, e.g., its halides and hydroxides, and its organic derivatives, such as, e.g., alkyl aluminates, preferably isopropyl aluminate.

The nitrogenous organic base can be an alkylammonium hydroxide, preferably tetrapropyl-ammonium hydroxide.

In case tetrapropylammonium hydroxide is used, the $TPA^+/SiO_2$ ratio (wherein TPA=tetrapropylammonium) of the reactants is comprised within the range of from 0.1 to 1, preferably from 0.2 to 0.4.

The reactants are reacted with each other by operating at a temperature of from 100° to 200° C., preferably of from 160° to 180° C., at a pH comprised within the range of from 9 to 14, preferably of from 10 to 12, and for a time period ranging from 1 hour to 5 days, preferably from 3 hours to 10 hours.

To the purpose of better illustrating the meaning of the present invention, some preparation and use examples are given, which in no way are to be considered as being limitative of the same invention.

EXAMPLE 1

This example shows the preparation of titanium-aluminum-silicalite.

0.3 g of aluminum isopropoxide is dissolved in 54 g of solution at 18.7% by weight of tetrapropyl-ammonium hydroxide.

In a separate vessel, 2.3 g of tetraethyl-orthotitanate is dissolved in 41.6 g of tetraethyl-silicate and this solution is added to the previously prepared one, with stirring.

The whole mass is heated at 50°-60° C., always with stirring, until a single-phase solution is obtained, then 100 cc of water is added.

The obtained solution is charged to an autoclave and is heated, under its autogenous pressure, at 170° C. over 4 hours.

The discharged product is centrifuged and washed twice by re-dispersion and centrifuging; it is then dried 1 hour at 120° C., and is then calcined 4 hours at 550° C. in the air.

The obtained product has an $SiO_2/Al_2O_3$ molar ratio of 98, and an $SiO_2/TiO_2$ molar ratio of 99, and is already in the $H^+$ form.

EXAMPLES 2-6

Table 1 other titanium-aluminum-silicalites are shown, which have been prepared by the same modalities as disclosed in Example 1, by varying the composition of the reactants, and the crystallization times.

The products obtained from Examples 2-5 are in the $H^+$ form, whilst the product obtained from Example 6 is in the $Na^+$ form; it can be turned, by the known processes, into its $H^+$ form. From the above-reported preparation examples, one can observe that the maximum amounts of titanium and aluminum which can be obtained in the end product are not independent from each other.

The minimum $SiO_2/TiO_2$ ratio which can be obtained in the product is of about 40, and it can be only obtained if $SiO_2/Al_2O_3$ ratio in the product is higher than about 120.

In order to obtain $SiO_2/Al_2O_3$ ratios lower than about 120, an increase in $SiO_2/TiO_2$ ratio must be accepted.

At $SiO_2/Al_2O_3$ molar ratios higher than 150 in the reaction mixture (Examples 1-5), the crystallization occurs, and with increasing $SiO_2/Al_2O_3$ ratios in the reactant mixture a decrease in $SiO_2/TiO_2$ ratio and an increase in $SiO_2/Al_2O_3$ ratio occurs in the obtained product.

$SiO_2/TiO_2$ ratio in the obtained product continues to decrease until it reaches its minimum value around 40, which is reached when $SiO_2/Al_2O_3$ in the reaction mixture is of from 300 to 400; further increases of $SiO_2/Al_2O_3$ ratio in the reactant mixture cause only $SiO_2/Al_2O_3$ to increase in the product, whilst $SiO_2/TiO_2$ remains nearly constant.

When the $SiO_2/Al_2O_3$ ratio in the reactant mixture is lower than or equal to 150, adding to the reaction mixture, to the purpose of obtaining the crystallization, salts and/or hydroxides of such cations as tetramethylammonium, ammonium alkali metals or alkali-earth metals (Example 6) is necessary.

These variations cause also an increase in $SiO_2/TiO_2$ ratio in the obtained product.

EXAMPLES 7-10

Always in Table 1, products are shown, which do not have the same characteristics as of the preceding products.

It can be observed from Examples 7, 8 and 9 that, when the molar composition of the reactant mixture is the following:

| | |
|---|---|
| $SiO_2/Al_2O_3 =$ | 100-150; |
| $SiO_2/TiO_2 =$ | 20; |
| $TPA^+/SiO_2 =$ | 0.25; |
| $H_2O/SiO_2 =$ | 40; | at a temperature of from 160° to 180° C. and under its autogenous pressure, the mixture does not crystallize.

It can be observed from Example 10 that, even if an alkali metal is added ($Na^+/SiO_2=0.04$), after 5 hours, the mixture does not crystallized, because the $SiO_2/Al_2O_3$ ratio in the reaction mixture is lower than or equal to 100.

EXAMPLE 11

Always in Table 1, the product of Example 11 is shown, which is obtained by starting from the same composition of the reactants of Example 10. It can be observed that after a crystallization time of 96 hours the mixture is crystallized.

Figure 3:
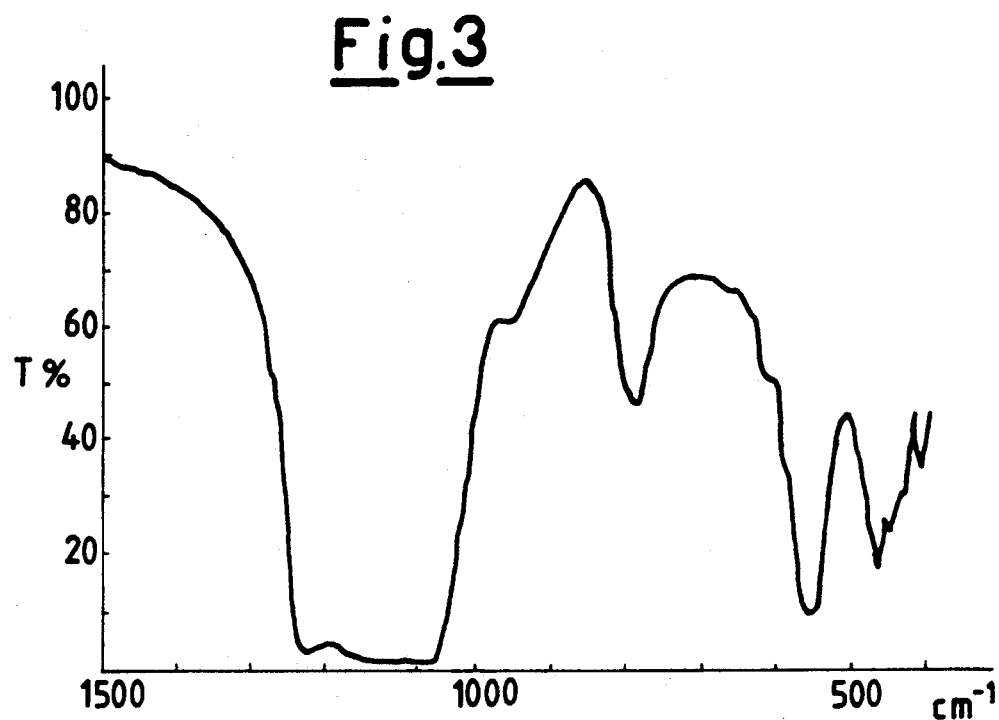
FIG. 3 is an IR spectrum of the product of Example 11.
Figure 4:
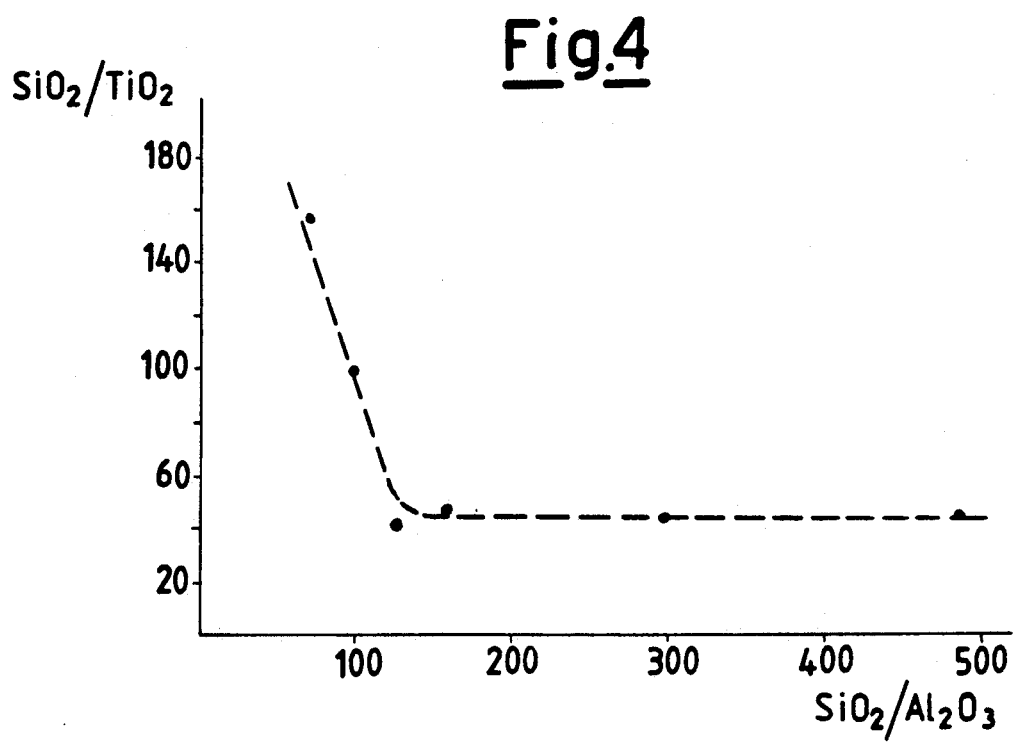
FIG. 4 is a chart showing the dependence between maximal, relative amounts of titanium and aluminum for the claimed invention.

The I.R. spectrum of this product, shown in FIG. 3, is not essentially equal to that shown in FIG. 1. From the spectrum of FIG. 3, it can be observed, in fact, that the band at 965-975 cm$^{-1}$ is present, but it has a much lower intensity than that represented in the spectrum of FIG. 1, although the product of Example 11 has a higher titanium contents. All of the above allows us to state that the addition of large amounts of alkali metals ($M^+/SiO_2 \geq 0.04$) in the reaction mass can cause an increase in titanium amount, which can be detected from the chemical analysis of the obtained product, an $SiO_2/TiO_2$ ratio lower than 40 being obtained, but is such case $TiO_2$ is at least partly in a form different from the form it has in the titanium-aluminum-silicalite according to the invention, and such as not to yield the spectrum of FIG. 1, but that of FIG. 3. In FIG. 4, a chart is shown, which sets forth the dependence of the maximum amounts of titanium (shown in the ordinates as $SiO_2/TiO_2$ molar ratio) and of aluminum (shown in the abscissae as $SiO_2/Al_2O_3$ molar ratio) which can be obtained in the end product.

EXAMPLE 12

To a tubular steel reactor, 1.04 g is charged of catalyst of 18-40 mesh of granulometry, prepared according to Example 2. The reactor is placed inside and electrical oven and is gradually heated up to the reaction temperature, with a stream of dimethyl ether being flown through it. The gaseous reaction products are analyzed by in-line chromatography after the liquid products being condensed in a bath kept at 0°-5° C. these latter are separately weighted and analyzed, always by chromatographic way. The conversion and selectivity are computed according to the hereunder shown equations:

$$\text{Conversion} = \frac{(DME_{in} - DME_{out})}{(DME_{in})}$$

$$\text{Selectivity} = \frac{(\text{mol of } i \text{ product})}{(DME_{in} - DME_{out})}$$

(DME = dimethyl ether; in = incoming; out = outgoing).

The reaction conditions and the results obtained are gathered in Table 2.

TABLE 2

| T | (°C.) | 320 | 342 |
|---|---|---|---|
| p | (atm) | 1 | 1 |
| GHSV | (h$^{-1}$) | 800 | 1600 |
| Run hours | | 4 | 4 |
| DME Conversion | (%) | 96.2 | 99.6 |
| Product Composition (% by weight - H$_2$O, DME excluded) | | | |
| CH$_3$OH | | 15.9 | 2.7 |
| CH$_4$ | | 0.4 | 0.2 |
| C$_2$H$_4$ | | 6.4 | 3.8 |
| C$_2$H$_6$ | | 0.01 | 0.04 |
| C$_3$H$_6$ | | 2.3 | 1.5 |
| C$_3$H$_8$ | | 0.7 | 0.8 |
| $\Sigma$C$_4$ | | 3.0 | 3.4 |
| $\Sigma$C$_5$ | | 0.9 | 0.6 |
| $\Sigma$C$_6$+ | | 70.3 | 86.9 |

EXAMPLE 13

To a small, 250-cc glass flask, there are charged, in the order as shown: phenol, 56.7 g; water, 8.4 g; acetone, 13.5 g; catalyst, prepared as in Example 2, 3 g.

The mixture is heated at 100° C. with stirring and under reflux, then, under the same conditions, within a minutes time, 10.5 g of 35% (weight/volume) H$_2$O$_2$ is added dropwise.

After 55 minutes from the beginning of the addition, all of H$_2$O$_2$ has been converted and the products are analyzed by gas-chromatography.

A yields of diphenols of

TABLE 1

| Example | Reaction Mixture Composition | | | | | Crystallization time, hours | Crystallization Temperature, °C. | Product Composition | |
|---|---|---|---|---|---|---|---|---|---|
| | SiO$_2$/Al$_2$O$_3$ | SiO$_2$/TiO$_2$ | Na$^+$/SiO$_2$ | TPA$^+$/SiO$_2$ | H$_2$O/SiO$_2$ | | | SiO$_2$/Al$_2$O$_3$ | SiO$_2$/TiO$_2$ |
| 1 | 250 | 20 | — | 0.25 | 40 | 4 | 170 | 98 | 99 |
| 2 | 300 | 20 | — | 0.25 | 40 | 3½ | 170 | 124 | 40 |
| 3 | 400 | 20 | — | 0.25 | 40 | 3 | 170 | 161 | 46 |
| 4 | 800 | 20 | — | 0.25 | 40 | 3 | 170 | 297 | 44 |
| 5 | 1200 | 20 | — | 0.25 | 40 | 3 | 170 | 462 | 43 |
| 6 | 150 | 20 | 0.005 | 0.25 | 40 | 4 | 170 | 65 | 155 |
| 7 | 150 | 20 | — | 0.25 | 40 | 5 | 170 | no crystallization | |
| 8 | 150 | 20 | — | 0.25 | 40 | 72 | 170 | no crystallization | |
| 9 | 100 | 20 | — | 0.25 | 40 | 5 | 170 | no crystallization | |
| 10 | 100 | 20 | 0.04 | 0.25 | 40 | 5 | 170 | no crystallization | |
| 11 | 100 | 20 | 0.04 | 0.25 | 40 | 96 | 170 | 45 | 18 | obtained diphenol mols = 0.08019

| charged H₂O₂ mol = | 0.099 | is obtained.

The residual amount of H$_2$O$_2$ is converted into pitches and O$_2$. On formed diphenols, ortho/para ratio is 1.18.

We claim:

1. Process for preparing a synthetic crystalline and porous material having a zeolite nature, containing oxides of silicon, titanium and aluminum, having, in its calcined and anhydrous state the empirical formula:

$$pHAlO_2 \cdot qTiO_2 \cdot SiO_2$$

wherein p has a value greater than zero and smaller than or equal to 0.050, and q has a value greater than zero and smaller than or equal to 0.025, the hydrogen of HAlO$_2$ being at least partially substitutable by cations, said process comprising: reacting under hydrothermal conditions a source of silicon, source of titanium, a source of aluminum and a nitrogenous organic base, with a SiO$_2$Al$_2$O$_3$ molar ratio in the reaction mixture greater than 150, with a SiO$_2$/TiO$_2$ molar ratio in the reaction mixture greater than 5, and with a H$_2$O/SiO$_2$ molar ratio from 10 to 100, at a temperature from 120° C. to 200° C., at a pH from 9 to 14 and for a time for 1 hour to 5 days.

2. The process according to claim 1, wherein in the reaction mixture the SiO$_2$/Al$_2$O$_3$ molar ratio is between 300 and 400, the SiO$_2$/TiO$_2$ molar ratio is between 15 and 25, and the H$_2$O/SiO$_2$ molar ratio is between 30 and 50.

3. The process according to claim 1, wherein said silicon source is selected from the group consisting of silica gel, silica sol and alkyl silicates, said titanium source is selected from the group consisting of salts and organic sources of titanium, said aluminum source is selected from the group consisting of salts and organic sources of aluminum.

4. The process according to claim 3, wherein said alkyl silicates are tetraethyl silicate.

5. The process according to claim 3, wherein said titanium salts are halides.

6. The process according to claim 3, wherein said organic sources of titanium are alkyl titanates.

7. The process according to claim 6, wherein said alkyl titanates are tetraethyltitanate.

8. The process according to claim 3, wherein said aluminum salts are selected from the group consisting of halides and hydroxides.

9. The process according to claim 3, wherein said organic sources of aluminum are alkyl aluminates.

10. The process according to claim 9, wherein said alkyl aluminates are isopropyl aluminate.

11. The process according to claim 1, wherein said nitrogenous organic base is alkylammonium hydroxide.

12. The process according to claim 11, wherein said alkylammonium hydroxide is tetrapropylammonium hydroxide.

13. The process according to claim 1, wherein said process occurs at a temperature from 160° C. to 180° C., at a pH from 10 to 12 and for a time ranging from 3 hours to 10 hours.

14. The process according to claim 12, wherein a TPA$^+$/SiO$_2$ molar ratio in the reaction mixture is from 0.1 to 1.

15. The process according to claim 14, wherein said TPA$^+$/SiO$_2$ molar ratio in the reaction mixture is from 0.2 to 0.4.

16. The process according to claim 1 wherein the reaction is conducted in the presence of one or more salts and/or hydroxides of alkali metals or alkaline earth metals, with a M$^+$/SiO$_2$ molar ratio wherein M$^+$ is an alkali-metal or an alkaline earth metal cation, smaller than 0.04.

17. The process according to claim 1 wherein a SiO$_2$/Al$_2$O molar ratio in the crystalline material higher than about 120 and a SiO$_2$/TiO$_2$ molar ratio in the crystalline material of about 40 is produced.

18. The process according to claim 16 wherein a SiO$_2$/Al$_2$O molar ratio in the crystalline material higher than about 120 and a SiO$_2$/TiO$_2$ molar ratio in the crystalline material of about 40 is produced.

* * * * *